(12) United States Patent
Marziliano et al.

(10) Patent No.: US 8,687,866 B2
(45) Date of Patent: Apr. 1, 2014

(54) METHODS AND SYSTEMS FOR PROCESSING IMAGES OF THE ANTERIOR CHAMBER ANGLE OF AN EYE

(75) Inventors: Pina Marziliano, Singapore (SG); Jing Tian, Singapore (SG); Hon-Tym Wong, Singapore (SG); Baskaran Mani, Singapore (SG); Tin Aung, Singapore (SG)

(73) Assignees: Nanyang Technological University, Singapore (SG); Tan Tock Seng Hospital PTE Ltd., Singapore (SG); Singapore Health Services Pte Ltd, Singapore (SG)

( * ) Notice: Subject to any disclaimer, the term of this patent is extended or adjusted under 35 U.S.C. 154(b) by 172 days.

(21) Appl. No.: 13/409,867

(22) Filed: Mar. 1, 2012

(65) Prior Publication Data

US 2012/0271288 A1    Oct. 25, 2012

Related U.S. Application Data

(60) Provisional application No. 61/449,380, filed on Mar. 4, 2011.

(51) Int. Cl.
*G06K 9/00* (2006.01)
*G01B 11/02* (2006.01)

(52) U.S. Cl.
USPC .......................... 382/128; 382/274; 356/497

(58) Field of Classification Search
USPC ......... 382/100, 103, 106–107, 128–134, 162, 382/168, 172, 173, 181, 194, 199, 221, 232, 382/254, 274, 276, 291, 305, 312; 604/521; 356/497; 435/6; 424/93.7; 514/6.5
See application file for complete search history.

(56) References Cited

U.S. PATENT DOCUMENTS

| 2003/0013087 | A1* | 1/2003 | Walter et al. ...................... 435/6 |
| 2008/0082078 | A1* | 4/2008 | Berlin ............................. 604/521 |
| 2011/0032533 | A1* | 2/2011 | Izatt et al. ...................... 356/497 |
| 2011/0294730 | A1* | 12/2011 | Shantha et al. ................ 514/6.5 |
| 2012/0237485 | A1* | 9/2012 | Du et al. ...................... 424/93.7 |

* cited by examiner

*Primary Examiner* — Seyed Azarian
(74) *Attorney, Agent, or Firm* — Merchant & Gould P.C.

(57) ABSTRACT

An optical coherence tomography (OCT) image of the anterior chamber of an eye is processed to determine automatically a location in the image corresponding to Schwalbe's line. First, the method finds the location of the corneal endothelium. Then the method fits a model to the detected corneal endothelium. Then the method determines the location of Schwalbe's line based on the relationship between the detected corneal endothelium and the fitted model, such as where the detected corneal endothelium diverges most from the fitted model. The Schwalbe's line is used to obtain a numerical measure of the anterior chamber angle of the eye. The method can be used in a process for screening patients for glaucoma. In the case of patients found to be suffering from glaucoma, treatment can be performed.

15 Claims, 10 Drawing Sheets

PRIOR ART

METHODS AND SYSTEMS FOR PROCESSING IMAGES OF THE ANTERIOR CHAMBER ANGLE OF AN EYE

This application claims benefit of Ser. No. 61/449,380, filed 4 Mar. 2011 in the United States and which application is incorporated herein by reference. A claim of priority, to the extent appropriate, is made.

FIELD OF THE INVENTION

The present invention relates to methods and systems for automatically processing images of the anterior chamber of the eye, and in particular HD-OCT (High definition optical coherence tomography) images, to obtain from them automatically information such as the location of Schwalbe's line, as part of a process for the an assessment of the Anterior Chamber Angle.

BACKGROUND OF THE INVENTION

Glaucoma is one of the most major eye diseases globally, and causes irreversible loss of vision due to the optic nerve damage leading to blindness. It is largely caused by poor filtration of aqueous fluid in the eyeball through the anterior chamber angle (ACA). If untreated, it leads to higher internal pressure, permanent nerve damage and blindness. It is the second leading cause of global blindness after cataract and is the leading cause of irreversible visual loss [1]. It accounts for 40% of blindness in Singapore [2].

There are two main types of glaucoma, depending on how the flow of fluid is blocked:

Open-angle glaucoma is caused by a gradual hype-functioning of the trabecular meshwork.

Figure 1:
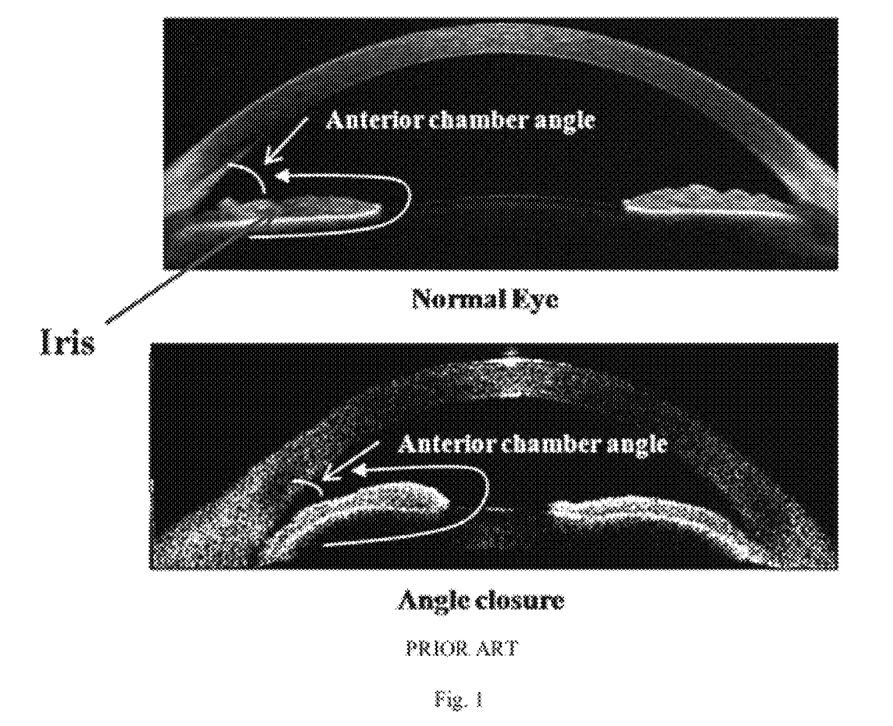
FIG. 1 is a diagram illustrating anterior chamber angle closure.

Angle-closure glaucoma (ACG) is caused by a change in the position of the iris, which then occludes the drainage channels. This is shown in FIG. 1, where the top left part indicates by a rectangular box the portion of the eye being considered, the top part of the figure represents a normal eye, and the lower part of the figure illustrates angle closure.

Glaucoma is asymptomatic in an early stage and is often only recognized when the disease is quite advanced and vision is lost. Detection of ACG in the early stage using clinical imaging modalities could lead to treatment to arrest its development or slow down the progression.

Anterior chamber angle assessment is used for the detection of ACG and is essential in deciding whether or not to perform laser iridotomy. Three approaches are used, namely, gonioscopy, ultrasound biomicroscopy (UBM) and anterior segment optical coherence tomography (AS-OCT).

Gonioscopy involves imaging with a contact lens placed onto the eye. Though considered as 'gold standard', gonioscopy is highly subjective. The definition of angle findings varies across grading schemes and there is no universal standard. It is also prone to potential measurement errors due to how the lens is placed on the eye [5] and different illumination intensities. It is also uncomfortable for the patient. As such, there are severe constraints to its potential as a screening tool.

Ultrasound biomicroscopy (UBM) uses a higher frequency transducer than regular ultrasound for more detailed assessment of the anterior ocular structures [6]. The different parameters defined in [7] to quantify ACA are as follows:

Angle opening distance (AOD): AOD 250/500 is the length of the line segment (referred as AOD line) drawn from a point which is 250/500 µm away from the scleral spur on the corneal endothelium, to the anterior surface of the iris in the normal direction of the endothelium. AOD 250 was first reported by [7] but is currently rarely used due to the high variability of the iris configuration at this location. In [8], AOD 500 is considered to be a better estimate of ACA.

Angle recess area (ARA): ARA refers to the area bounded by corneal endothelium, the iris and the AOD line at 500 or 750 µm.

Trabecular iris space area (TISA): TISA is the area between the scleral spur and the AOD line. The TISA modifies the ARA by removing the area anterior to scleral spur.

Ishikawa et al. designed a semi-automated program (UBM Pro2000) [9] to calculate several important parameters, i.e. AOD 250, 500 and ARA 750, based on the manual identification of the scleral spur, which is prone to intra-observer and inter-observer variability. Although UBM is useful in quantifying the ACA, the equipment is costly and the resolution is sometimes unsatisfactory. Furthermore, it is neither user nor patient friendly as a water bath is needed to image the eye [5].

AS-OCT is another instrument for imaging the anterior chamber angle. Optical coherence tomography is analogous to ultrasound imaging, as the image is formed by detecting the signal backscattered from different tissue structures. Instead of sound waves, light is used for OCT imaging, which avoids the need for direct contact with the eyes to transmit or receive the signal. Furthermore, the use of light achieves higher spatial resolution than ultrasound. From the experiments in [10], AS-OCT is found to be at least as sensitive in detecting angle closure when compared with gonioscopy.

The existing angle assessment parameters used in AS-OCT remain the same as UBM images. The current Visante™ built-in angle assessment software requires substantial user labeling, i.e. the scleral spur, cornea and iris, hence the measurements are subjective. The Zhongshan Angle Assessment Program [11] is able to define the borders of the corneal epithelium, endothelium and iris to measure AOD, ARA and TISA using the location of scleral spur as the only observer input. However, it is found that the scleral spur is not identified in 20% to 30% of Visante™ OCT images and measurements using the scleral spur as the landmark are subjective to intra-observer and inter-observer variability and so are not very reproducible.

With the advancement in OCT imaging technology, higher resolution images could be produced in shorter time. Zeiss Cirrus™ HD-OCT [12] uses spectral domain technology to achieve image acquisition speed of 27,000 axial scans per second, which results in approximately 50 times faster data acquisition in practice as compared to the time-domain Visante™ OCT. Furthermore, the transverse resolution of HD-OCT images is improved from 60 µm/pixel to 15 µm/pixel and axial resolution is improved from 18 µm/pixel to 5 µm/pixel [13], [14]. However, as Cirrus™ uses a shorter wavelength (840 nm) than Visante™ (1310 nm) to achieve better spatial resolution, the penetration depth is decreased.

Figure 2:
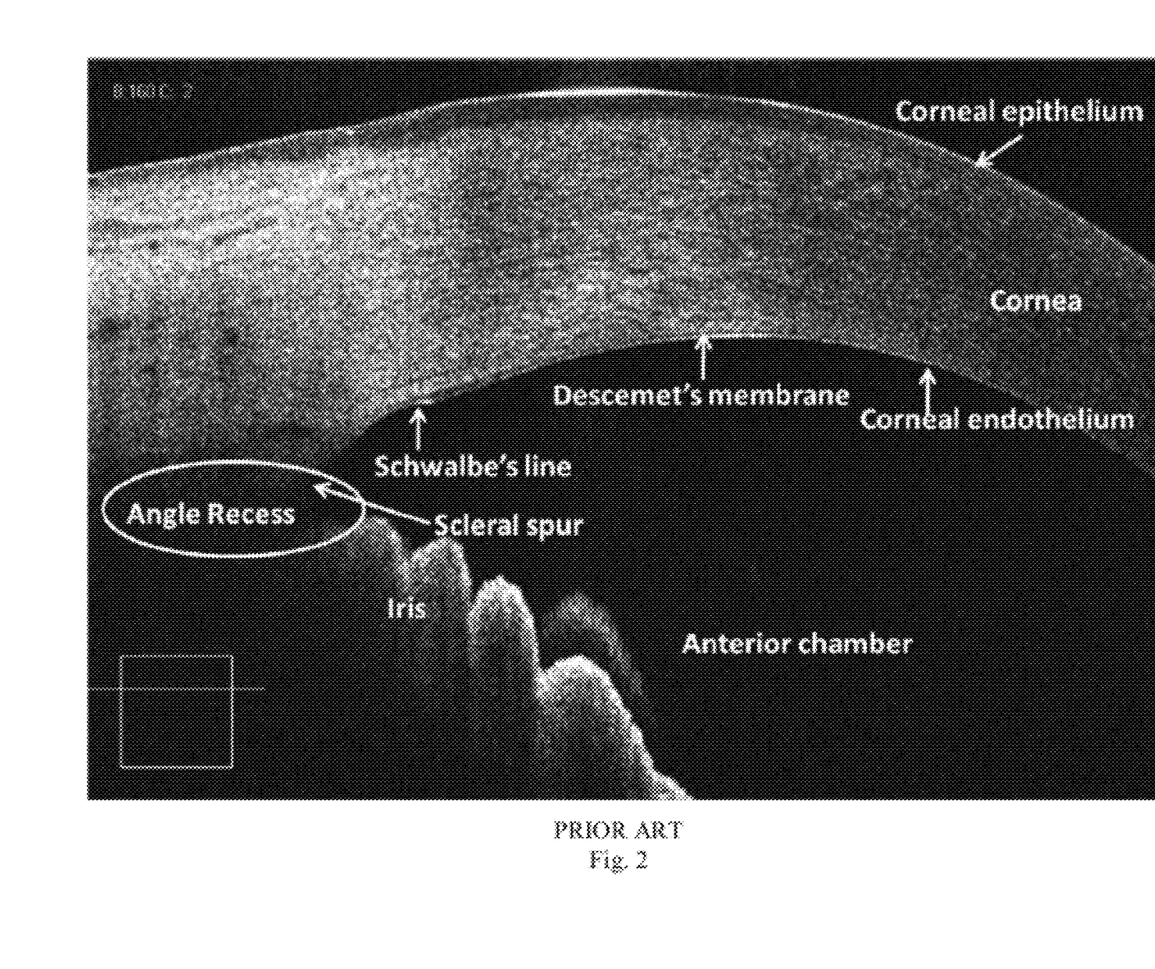
FIG. 2 is a HD-OCT image showing the locations of certain elements of the anterior chamber of an eye.

FIG. 2 show an anterior segment HD-OCT images. It is marked to illustrate the locations of the angle recess (the region between the cornea and the iris), the scleral spur (the point where the curvature of the angle wall changes, often appearing as an inward protrusion sclera), the corneal endothelium (the inner-most layer of cornea), the coneal epithelium (the outer-most layer of the cornea), Descemet's membrane (the second innermost layer), and Schwalbe's line (the termination of Descemet's membrane). As illustrated in FIG. 2, the angle recess is obscured in shadow and the scleral spur is not well defined in the HD-OCT image [15] due to the scattering by the sclera [14]. On the other hand, Schwalbe's line, which marks the termination of Descemet's membrane, can be identified in more than 90% of HD-OCT images [15].

SUMMARY OF THE INVENTION

An object of the present invention is to make possible automatic processing of an optical coherence tomography image of the anterior chamber of an eye, and in particular an HD-OCT image.

A further object of the invention is the automatic identification of Schwalbe's line in an HD-OCT image, and the use of this novel landmark to provide a more reliable and consistent way of quantifying the anterior chamber angle in an HD-OCT image.

In general terms the invention proposes that a location in an OCT image corresponding to Schwalbe's line (i.e. a point in the OCT image corresponding to the landmark in the eye at which Schwalbe's line intersects with the plane in which the OCT image was a captured) is detected automatically by: detecting the location of the corneal endothelium; fitting a model to the detected corneal endothelium; and determining the location of Schwalbe's line based on the relationship between the detected corneal endothelium and the fitted model, such as where the detected corneal endothelium diverges most from the fitted model.

The detection of the Schwalbe's line is part of a process for obtaining data indicative of the anterior chamber angle, i.e. one or more numerical measures of the angle. That process may be used to screen patients reliably for reduced anterior chamber angle using optical coherence tomography images, and without gonioscopy or ultrasound biomicroscopy. Patients with reduced anterior chamber angle may be identified for further testing and/or treatment. Such treatment may include laser iridotomy. The effect of the treatment may be monitored using OCT images captured periodically, and the images may be processed according to the invention.

The detection of the corneal endothelium may include a thresholding step applied to the image, to identify first pixels having an intensity to one side of the threshold (e.g. above the threshold) and second pixels having an intensity on the other side of the threshold (e.g. below the threshold). Naturally, it would be equivalent to obtain a negative version of the OCT image, and perform thresholding swapping the meanings of "above" and "below".

The term "automatic" is used here in the sense that it is substantially without human interaction, except as to the initialization of the algorithm.

Although the embodiments of the invention described below use a single OCT image captured in a single plane, there are possible applications of the invention to datasets having multiple OCT images for a single eye, such as a three-dimensional dataset composed of multiple OCT images in different respective planes, e.g. parallel spaced-apart planes. Each of the planes may have a different respective intersection with Schwalbe's line.

BRIEF DESCRIPTION OF THE DRAWINGS

Embodiments of the invention will now be described for the sake of example only with reference to the following figures, in which.

FIRST EMBODIMENT

1. Explanation of the First Embodiment

Figure 3:
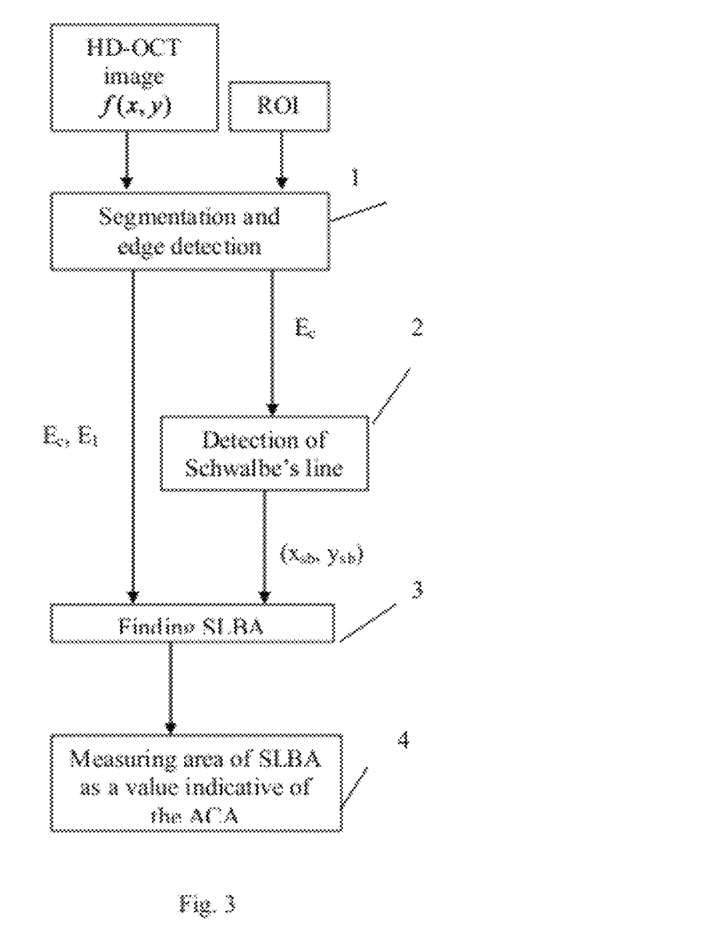
FIG. 3 is a flow diagram of a first embodiment of the invention.

A block diagram of the first embodiment of the invention is given in FIG. 3. The input to the method is an HD-OCT image denoted by $f(x,y)$ and a region of interest ROI. Since the scleral spur cannot be clearly distinguished, the embodiment relies on the automatic detection of Schwalbe's line which is located on the inner surface of the cornea and marks the termination of Descemet's membrane. In a step 1, the embodiment segments the cornea and the iris, and extracts the edge of the cornea. In step 2 it uses linear regression to fit a model to the edge of the cornea, and identifies the location of Schwalbe's line as the point at which there is a maximum distance between the points on the cornea and the regression line. In step 3, Schwalbe's Line Bounded Area (SLBA) is obtained by finding the triangular area enclosed within the cornea and the iris. This permits ACA measurement in step 4, by measuring the area of the SLBA which is informative about the ARA. The details of the methodology are explained in the following subsections.

1.1 Segmentation and Edge Detection In step 1, the cornea and the iris regions are extracted by an image segmentation method, and then the inner surface of the cornea and the upper boundary of the iris are detected.

Figure 4:
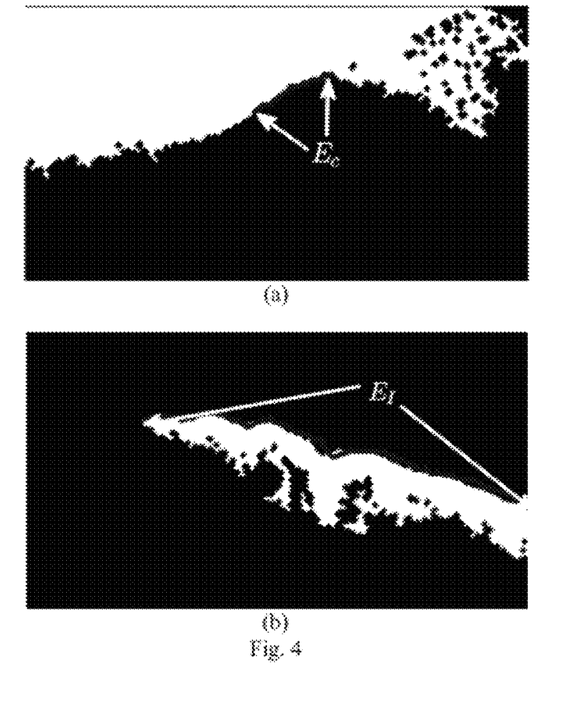
FIG. 4 shows two connected components extracted by the first embodiment of the invention, corresponding respectively to (a) Cornea $q_c(x,y)$ and (b) Iris $q_I(x,y)$.

First, we convert the input HD-OCT image $f(x,y)$ of dimension M×N to a binary image defined by $$g(x, y) = \begin{cases} 1 & \text{if } f(x, y) > \text{threshold}, \\ 0 & \text{Otherwise} \end{cases} \quad (1)$$

where the threshold can be calculated by Otsu's method [21], in which the intra class variance is minimized and the inter class variance is maximized. The cornea and the iris can be separated by the connected component labeling [17] segmentation method. The basic idea of this method is to scan the image and group its pixels into components based on connectivity and assign each component with a unique label. The components with the largest and the second largest number of pixels are identified as the cornea, $q_c(x,y)$, and the iris, $q_I(x,y)$, respectively. These segmented binary images are illustrated in FIGS. 4(a) and (b), respectively.

A rectangular region of interest (ROI) is identified and defined by

ROI=$[x_L+w] \times [y_T, y_T+h]$, where $(x_L, y_T)$ are the coordinates of the top left corner of the rectangle and w and h specify its width and height. The Region of Interest (ROI) is a rectangular area provided by the user and includes the location of Schwalbe's line. The size of the window is 50×50 pixels. Although it is a user input, we have found the results of the algorithm are usually not affected by the exact choice of the ROI as long as the Schwalbe's line is located inside the ROI.

It is assumed that Schwalbe's line is located inside the region of interest, thus the lower boundary of the cornea is defined by $$E_c = \{(x,y) | g_c(x,y)=1 \text{ and } g_c(x,v)=0, \forall (x,y) \in ROI \text{ with } v > y\} \quad (2)$$

and the upper boundary of the iris is defined by $$E_I = \{(x,y) | g_I(x,y)=1 \text{ and } g_I(x,v)=0 \ \forall v > y\} \quad (3)$$

1.2 Auto-Detection of Schwalbe's Line

In step 2, using linear regression, the embodiment first determines a linear function $l_c(x) = m_c x + b$ which best fits the points on the lower boundary of the cornea, that is, $$\min_{m_c, b_c} \|y - l_c(x)\|^2, (x, y) \in E_c \quad (4)$$

and then the location of Schwalbe's line is the point at which there is a maximum distance between the points in $E_c$ and the regression line $l_c(x)$, that is, $$(x_{sb}, y_{sb}) = \arg \max(l_c(x) - y), (x,y) \in E_c \quad (5)$$

Figure 5:
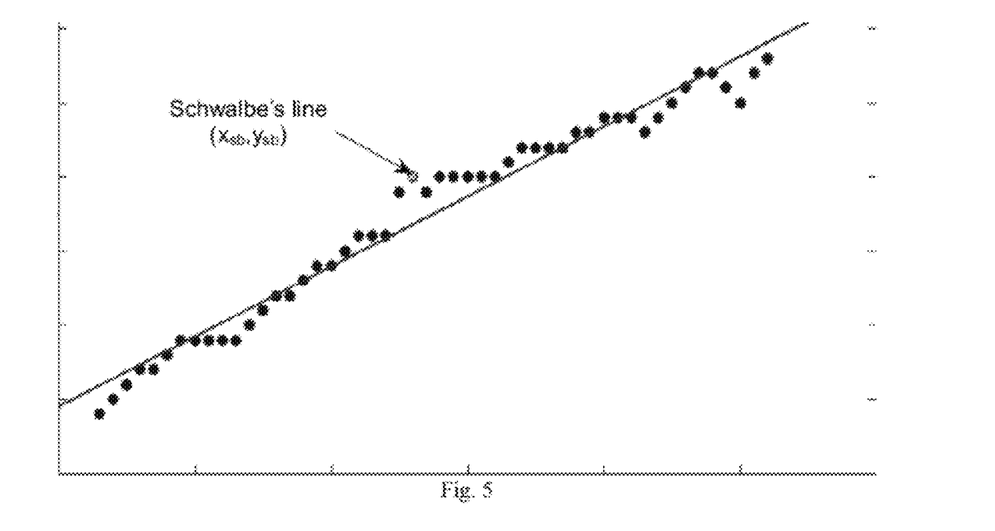
FIG. 5 shows a process for the detection of Schwalbe's line in the first embodiment.

FIG. 5 illustrates that Schwalbe's line is the point with maximum difference between the set of points in $E_c$ (which are shown as dots) and the corresponding regression line 1 (x) (which is shown as the solid line).

1.3 Schwalbe's Line Bounded Area (SLBA)

As illustrated in FIG. 4, the lower boundary of the cornea and the upper boundary of the iris do not intersect, i.e. $E_c \cap E_I = \emptyset$. To define an area the embodiment first finds a linear regression for each set of points and then extends the curves so as to form the anterior chamber angle (ACA). Schwalbe's Line Bounded Area (SLBA) is obtained by finding the area enclosed within the following three lines:

1) The line segment on the cornea before Schwalbe's line: $l_{c_2}(x) = m_2 x + b_2$ such that $$\min_{m_2, b_2} \|y - l_{c_2}(x)\|^2, (x, y) \in E_c \text{ and } x < x_{sb} \quad (6)$$

2) The upper boundary of the iris and the regression line segment obtained from the points in $E_I$:

$$l_I(x) = \begin{cases} y & (x,y) \in E_I \\ m_I x + b_I & (x,y) \notin E_I \end{cases} \quad (7)$$

Where $$\min_{m_I, b_I} \|y - m_I x + b_I\|^2, (x, y) \in E_I \quad (8)$$

3) The line segment which starts from Schwalbe's line and is perpendicular to $l_{c_2}$:

$$l_b(x) = -\frac{1}{m_2}(x - x_{sb}) - y_{sb} \quad (9)$$

Figure 6:
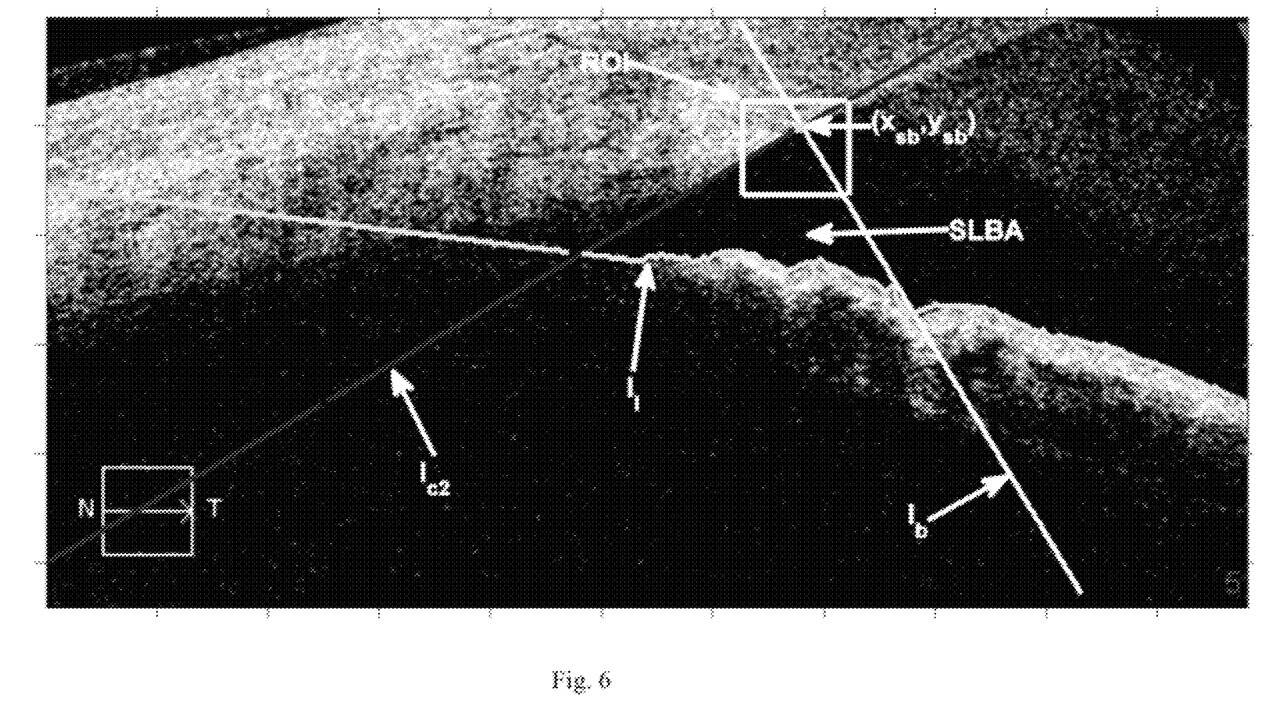
FIG. 6 illustrates an "SLBA" area of an HT-OCT derived by the first embodiment.

The three detected boundaries, $l_{c_2}$, $l_I$ and $l_b$, of the SLBA triangle are annotated in FIG. 6. SLBA mimics the filtration space and access zone directly in front of the ACA.

1.4 Find the Area of the SLBA

In step 4 the area of the SLBA is found, which is a value indicative of the value of the ACA. A small SLBA value suggests the possibility of angle-closure glaucoma. The proposed parameter uses area to quantify the ACA, which is similar to ARA and TISA. But Schwalbe's line is more distinct in HD-OCT images and hence, SLBA is a more reliable parameter to quantify angle closure glaucoma.

2 Data, Experiments and Results

We now turn to experimental text of the embodiment. HD-OCT images were captured using Cirrus™ [12] under dark room conditions at the Tan Tock Seng Hospital Eye Center, Singapore and the implementation of the algorithm was done in Matlab™ 2008a using an Intel® Core™ 2 Quad CPU Q9400 @266 GHz and 267 GHz computer. The embodiment was tested on a data set consisting of ten images labeled $f_n$, n=1, 2, . . . 10 with pixel resolution M×N ranging from 540×270 to 1815×1126 and the identified Region of Interest is a 50×50 square in the neighborhood of Schwalbe's line. FIG. 6 shows the result for $f_{10}$. The error measurements between the detected values for Schwalbe's line using the first embodiment, $(x_{sb}, y_{sb})$ and corresponding values identified by the ophthalmologist, $(x_{sb}', y_{sb}')$ are defined by $$(\epsilon_x, \epsilon_y) = \left( \left| \frac{(x_{sb} - x_{sb}') \times a}{M} \right|, \left| \frac{(y_{sb} - y_{sb}') \times b}{N} \right| \right) \quad (10)$$

where a=7.2 mm and b=2.7 mm are the horizontal and vertical scales of the images, respectively. The results are summarized in Table I.

TABLE 1

| | $f_n$ | | | | | | | | | |
|---|---|---|---|---|---|---|---|---|---|---|
| | $f_1$ | $f_2$ | $f_3$ | $f_4$ | $f_5$ | $f_6$ | $f_7$ | $f_8$ | $f_9$ | $f_{10}$ |
| $\epsilon_x$ | 0.056 | 0.013 | 0.023 | 0.038 | 0.029 | 0.086 | 0.067 | 0.000 | 0.067 | 0.027 |
| $\epsilon_y$ | 0.000 | 0.030 | 0.013 | 0.011 | 0.000 | 0.005 | 0.000 | 0.036 | 0.022 | 0.001 |

The average values of $\epsilon_x$ and $\epsilon_y$ are 0.0388 mm, 0.00945 mm, respectively, which corresponds to less than 0.5% and 0.35% of the image dimension in each direction. Thus, the value of Schwalbe's line obtained with our algorithm faithfully agrees with the ophthalmologist's manual identification. The algorithm's average processing time is about 0.111 seconds.

Second Embodiment

1. Explanation of the Second Embodiment

Figure 7:
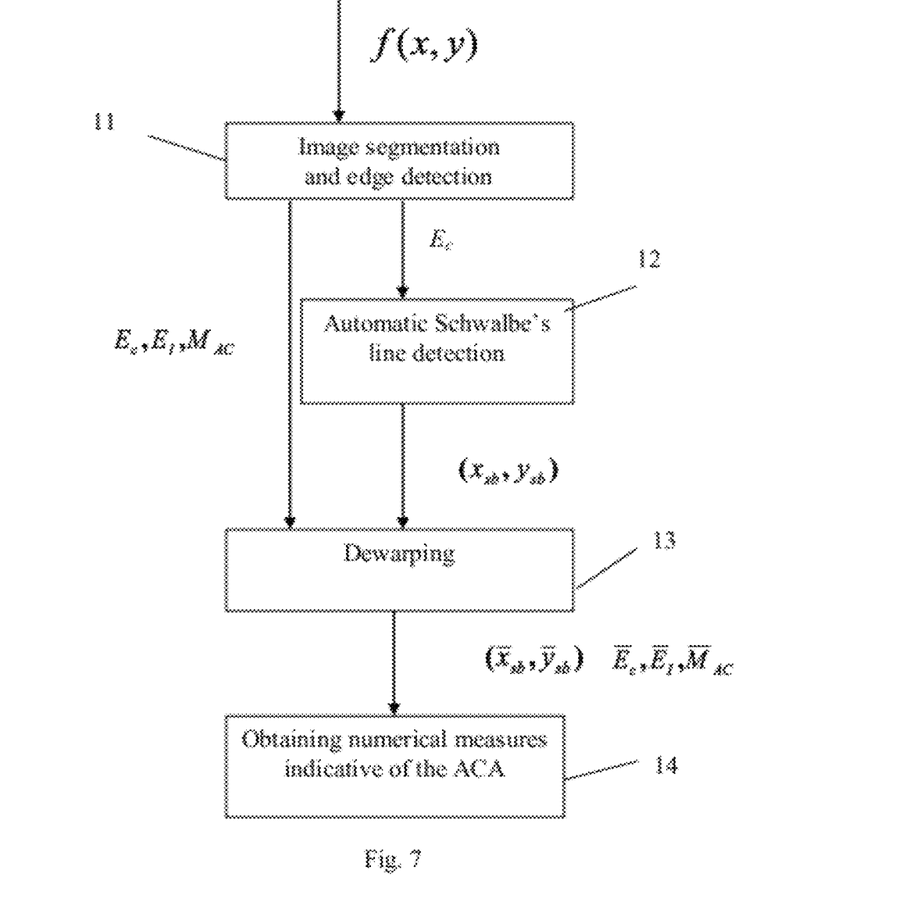
FIG. 7 illustrates the steps of a second embodiment of the invention.

A block diagram of the second embodiment is given in FIG. 7. First there is a step 11 of image segmentation and line detection, then there is a step 12 of automatic detection of Schwalbe's line, then a step 13 of dewarping, and finally a step 14 of assessing angles. These steps are explained in more detail below.

The definitions of the variables used in this explanation are as follows:

Original grayscale image: $f(x,y), (x,y) \in [1,M] \times [1,N]$;

Resized image: $f'(x,y), (x,y) \in [1,\overline{M}] \times [1,\overline{N}]$;

Scan width and depth: w and d;

Segmentation threshold to detect anterior chamber and corneal epithelium: $T_a$ and $T_p$;

Corneal endothelium, anterior surface of the iris and anterior chamber mask in $f(x,y)$: $E_c$, $E_I$ and $M_{AC}$;

Corneal endothelium, anterior surface of the iris and anterior chamber mask after dewarping: $\overline{E_c}$, $\overline{E_I}$ and $\overline{M}_{AC}$;

Corneal epithelium: $E_p$;

Automatically detected and manually labeled Schwalbe's line: $(x_{sb}, y_{sb})$ and $(x_{sb}^0, y_{sb}^0)$;

Angle Opening distance of Schwalbe's line based on $(x_{sb}, y_{sb})$ and $(x_{sb}^0, y_{sb}^0)$ respectively: $AOD_{sb}$ and $AOD_{sb}^0$;

Angle Recess Area bounded by Schwalbe's line based on $(x_{sb}, y_{sb})$ and $(x_{sb}^0, y_{sb}^0)$ respectively: $ARA_{sb}$ and $ARA_{sb}^0$;

Trabecular iris space area bounded by Schwalbe's line based on $(x_{sb}, y_{sb})$ and $(x_{sb}^0, y_{sb}^0)$ respectively: $TISA_{sb}$ and $TISA_{sb}^0$.

1.1 Image Segmentation & Edge Detection

The grayscale image $f(x,y)$ is first segmented into two sets of pixels, the foreground object (B) and the background object ($\hat{B}$):

$$B = \{(x,y) | f(x,y) > T_a, (x,y) \in [1,M] \times [1,N]\}$$

$$\hat{B} = \{(x,y) | f(x,y) \leq T_a, (x,y) \in [1,M] \times [1,N]\}$$

where $T_a$ is a threshold used to segment the image. $T_a$ is selected experimentally (it is selected as 40 in the experiments below). Morphological operations, e.g. erosion, dilation, opening and closing [16], are performed to remove the speckle noise.

Using the method described in [17], components of B and $\hat{B}$ are labeled as $\{B_1, B_2, \ldots, B_k\}$ and $\{\hat{B}_1, \hat{B}_2, \ldots, \hat{B}_k\}$ such that $|B_1| > |B_2| > \ldots > |B_k|$ and $C_x(\hat{B}_1) > C_x(\hat{B}_2) > \ldots > C_x(\hat{B}_k)$, where $|\cdot|$ and $C_x(\cdot)$ denote the cardinality (the number of pixels) and the x-coordinate of the centroid of a component, respectively.

The following segmentation and edge detection algorithm ("Algorithm 1") is then performed:

Algorithm 1 if $|B_2|/|B_1| < 0.01$ then the cornea is assumed to be connected to the iris, so 1. Define the $M_{AC}$ as $M_{AC} = \hat{B}_1$
2. Perform edge detection to obtain two edges:

$$E_c = \{(x,y) | (x,y) \in M_{AC}, (x,v) \notin M_{AC}, \forall v < y\}$$

$$E_I = \{(x,y) | (x,y) \in M_{AC}, (x,v) \notin M_{AC}, \forall v > y\}$$

else

1. Perform edge detection $$E_c = \{(x,y) | (x,y) \in B_1 \text{ and } (x,v) \notin B_1, \forall v < y\}$$

$$E_I = \{(x,y) | (x,y) \in B_2 \text{ and } (x,v) \notin B_2, \forall v < y\}$$

2. Find $M_{AC}$ from $$M_{AC} = \{(x,y) | v < y < u, \text{ where } (x,u) \in E_c \text{ and } (x,v) \in E_I\}$$

end if

Figure 8:
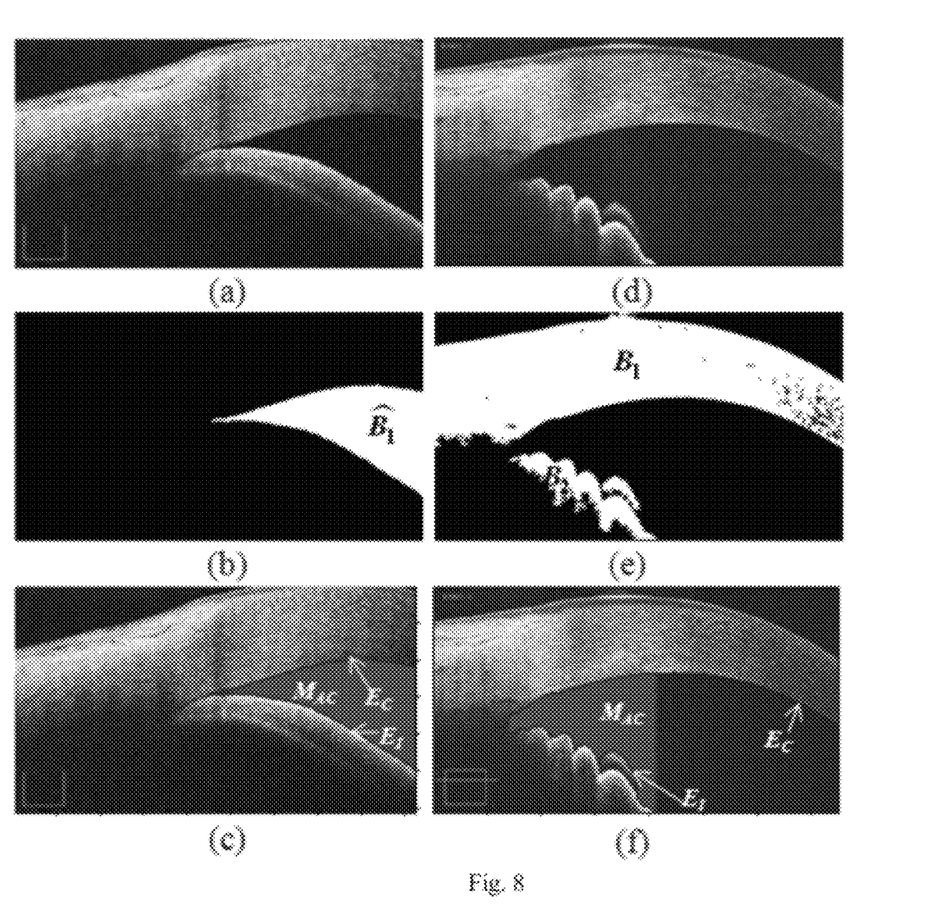
FIG. 8 illustrates the operation of a first step of the second embodiment of the invention in two scenarios illustrated respectively by FIG. 8(a)-(c) and FIG. 8(d)-(f)

In other words, algorithm 1 first determines whether the cornea is connected or disjoint from the iris. It assumes that it is connected if $|B_2|/|B_1| < 0.01$, implying that the area of the object $B_2$ is insignificant as compared with that of $B_1$, and $B_2$ is classified as noise. This is the situation illustrated in FIGS. 8(a)-8(c). FIG. 8(a) shows the original image $f(x,y)$. This has a single large connected foreground region, so $|B_2|/|B_1| < 0.01$. FIG. 8(b) shows that in this case $M_{AC}$ is chosen as $\widehat{B_1}$, i.e. the background component with the right-most centroid. Note that the embodiment uses the right-most centroid (rather than the left-most centroid) because it assumes that the images are the temporal scans of the left eye or the nasal scans of the right eye 1. $E_c$ and $E_I$ are then chosen as the upper boundary and lower boundary of $M_{AC}$ respectively. Note that if the image is the nasal scan of the left eye or the temporal scan of the right eye, we need to flip the image horizontally before the segmentation, or alternatively the left-most centroid is taken as $\hat{B}_1$ instead in Algorithm 1.

Conversely, if $|B_2|/|B_1| < 0.01$ then the cornea and iris are disjoint. This is the situation illustrated in FIG. 8(d)-(f). In this case, it is assumed that $B_1$ and $B_2$ are the cornea and the iris respectively. Thus $E_c$ and $E_I$ are detected as the lower boundary of $B_1$ and the upper boundary of $B_2$, respectively, and the region between is $M_{AC}$.

1.2 Automatic Detection of Schwalbe's Line

It is found that $E_c$ has a very good fit to fourth order polynomial $p(x) = p_4 x^4 + p_3 x^3 + p_2 x^2 + p_1 x + p_0$ where $p_4$, $p_3$, $p_2$, $p_1$ and $p_0$ are real numbers. This is true except for the region around Schwalbe's line, where the curvature of $E_c$ changes suddenly due to the termination of Descemet's membrane. Although it would be possible in principle to use a polynomial of yet higher degree, the fit is hardly improved for higher powers of x than 4. Based on this observation, we develop a method to detect Schwalbe's line automatically ("Algorithm 2"):

Algorithm 2

Figure 9:
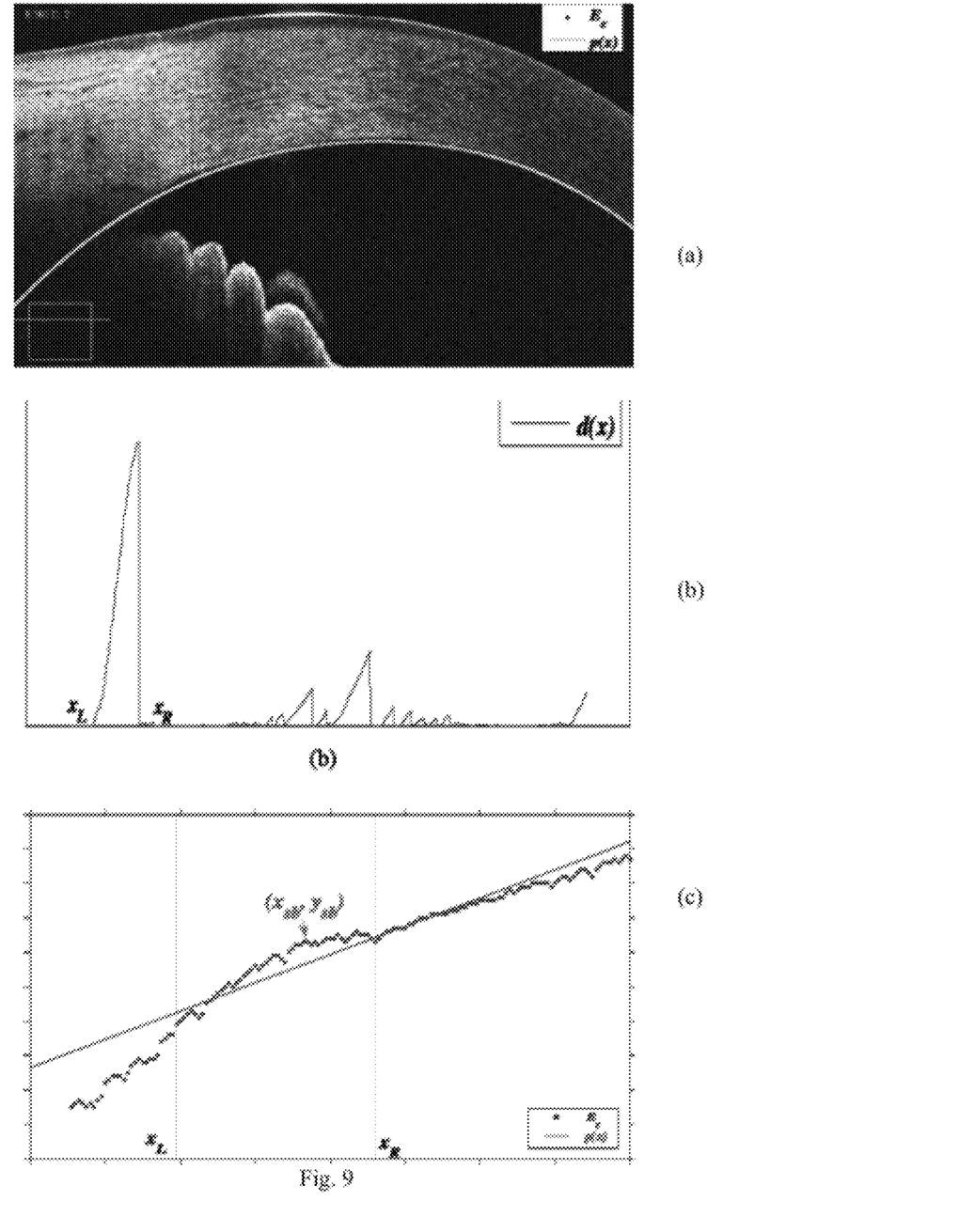
FIG. 9 is composed of FIGS. 9(a) to 9(c), and illustrates the operation of a second step of the second embodiment.

1. $E_c$ is first fitted to the fourth order polynomial $p(x) = p_4 x^4 + p_3 x^3 + p_2 x^2 + p_1 x + p_0$ where $$(p_4, p_3, p_2, p_1, p_0) \underset{(p_4, p_3, p_2, p_1, p_0)}{\operatorname{argmin}} \left\{ \sum_{(x,y) \in E_c} (p(x) - y)^2 \right\}$$

as shown in FIG. 9(a).

2. A window region containing Schwalbe's line is detected automatically in this step. Consider $$d(x) = \int_{b(x)}^{x} H(p(u) - v) \cdot (p(u) - v) du,$$

where $H(\bullet)$ is the Heaviside step function, $(u,v) \in E_c$ and $$b(x) = \max\{u | u < x, p(u) \le v, (u,v) \in E_c\}$$

Note that although this expression is given here as an integral, since $E_c$ is known only at a set of points, the integral is actually a summation over those points.

As illustrated in FIG. 9(b), the boundaries of the window region containing Schwalbe's line are $$x_R = \underset{x}{\operatorname{argmin}} d(x)$$

$$x_L = b(x_R).$$

3. The regression line of $E_c$ around the neighborhood of $x_R$ is $l_c(x) = m_c x + b_c$, where $$(m_c, b_c) = \underset{(m_c, b_c)}{\operatorname{argmin}} \sum_{x=x_R}^{x_R + \Delta} (y - l_c(x))^2,$$

and where $\Delta$ is the size of the neighborhood, i.e. $x_R - x_L$. That is, the regression is over points outside the window, and just to the right of the window.

4. Schwalbe's line, $(x_{sb}, y_{sb})$, is the point at which there is a maximum distance between $l_c$ and $E_c$ as seen in FIG. 9(c):

$$(x_{sb}, y_{sb}) = \underset{(x,y)}{\operatorname{argmin}}(l_c(x) - y), x \in [x_L, x_R]$$

1.3 Dewarping

The optical coherence tomography images are distorted as light changes direction at the interface between the air and the cornea. Moreover, the OCT records the optical path length that the light travels, not the actual physical distance. So both the directions and physical distance need to be corrected before making any measurements.

Westphal [18] corrected the scanning geometry (convergent or divergent) and proposed a backward transformation approach for refraction correction based on Fermat's Principle. However, the user needs to input several points on the corneal epithelium to perform active contour in the refraction correction step of the algorithm. Dewarping remains a subjective and time-consuming process.

The second embodiment includes a step 13 of automatic edge detection of the corneal epithelium in the dewarping process to avoid the need for user input. There are three steps in the dewarping algorithm: (1) Resizing f(x,y) so that the axial and transverse resolutions are the same; (2) Automatic detection of the corneal epithelium and (3) Refraction correction using Snell's law.

The details of the steps are as follows:

1) Resizing: The original HD-OCT image $f(x,y):(x,y) \in [1, M] \times [1, N]$ is resized to $f'(x_r, y_r),(x_r, y_r) \in [1, \overline{M}] \times [1, \overline{N}]$; such that $$\frac{\overline{M}}{w} = \frac{\overline{N}}{d},$$

where w and d are the scan width and depth, respectively. Hence, the axial resolution and transverse resolution are the same. The point (x,y) on the original image is mapped to $(x_r, y_r)$ in the resized image as defined by the following transformation:

$$(x_r, y_r) = (T_x(x), T_y(y)) = \left(\frac{\overline{M}}{M} x, \frac{\overline{N}}{N} y\right)$$

Figure 10:
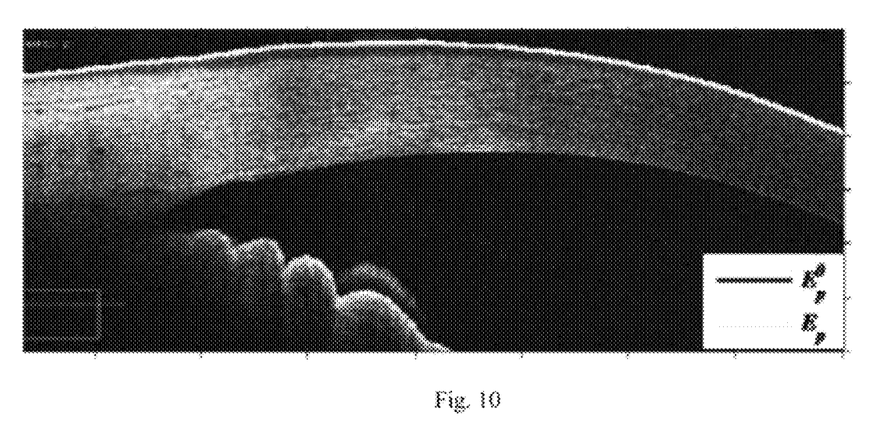
FIG. 10 illustrates a sub-step of a third step of the second embodiment.

2) Corneal epithelium detection: Using a similar method to described in Section 1.1, the cornea region in $f'(x_r, y_r)$ is identified using a connected component labeling method, and the upper boundary of the cornea $E_p^0$ is initially taken as the corneal epithelium. However, the embodiment removes any sudden change caused by non-uniform illumination as illustrated in FIG. 10. Lastly, a fourth order polynomial $q(x_r)$ is used to interpolate the points in $E_p^0$. (As in step 1, the fourth order polynomial fits $E_p^0$ so well that a fifth order polynomial does little better, so a fourth order polynomial is sufficient for the fitting). The details of the corneal epithelium detection algorithm are as follows ("Algorithm 3"):

Algorithm 3

1. In an Image Segmentation substep, the embodiment converts the image $f'(x_r, y_r)$ to a binary image using $T_p$ as the threshold and labeling the components $\{B_1^r, B_2^r, \ldots, B_k^r\}$, such that $|B_1^r| > |B_2^r| > \ldots > |B_3^r|$. $B_1^r$ is taken as the cornea component.

2. In an initial edge detection substep, is defined by $$E_p^0 = \{(x_r, y_r) | (x_r, y_r) \in B_1^r, (x_r, v_r) \notin B_1^r, \forall v_r < y_r\}$$

3. In a sub-step of removing any sudden change of $E_p^0$, the embodiment removes the sample points of $E_p^0$ between $x_s$ and $x_e$ where $$x_s = \min\{x | \|y_r(x_r) - y_r(x_r - 1)\| > \delta, (x_r, y_r) \in E_p^0\}$$

$$x_e = \max\{x | \|y_r(x_r) - y_r(x_r - 1)\| > \delta, (x_r, y_r) \in E_p^0\}$$

$\delta$ is the threshold value to define the sudden change, and it is set to 5 during the experiments reported below.

4. In an interpolation sub-step, the embodiment interpolates the points in using fourth order polynomial $q(x_r) = q_4 x_r^4 + q_3 x_r^3 + q_2 x_r^2 + q_1 x_r + q_0$, such that for $(x_r, y_r) \in E_p^0$, $$(q_4, q_3, q_2, q_1, q_0) = \underset{(q_4, q_3, q_2, q_1, q_0)}{\operatorname{argmin}} \sum_{(x_r, y_r) \in E_p^0} (q(x_r) - y_r)^2$$

5. Finally, a final estimate of the position of the corneal epithelium, $E_p$ is defined by $E_p = \{(x_r, y_r) | x_r \in [1, \overline{M}], y_r = q(x_r)\}$. FIG. 10 shows the initial detected corneal epithelium $E_p^0$, and the final estimate of the position of the corneal epithelium, $E_p$.

Figure 11:
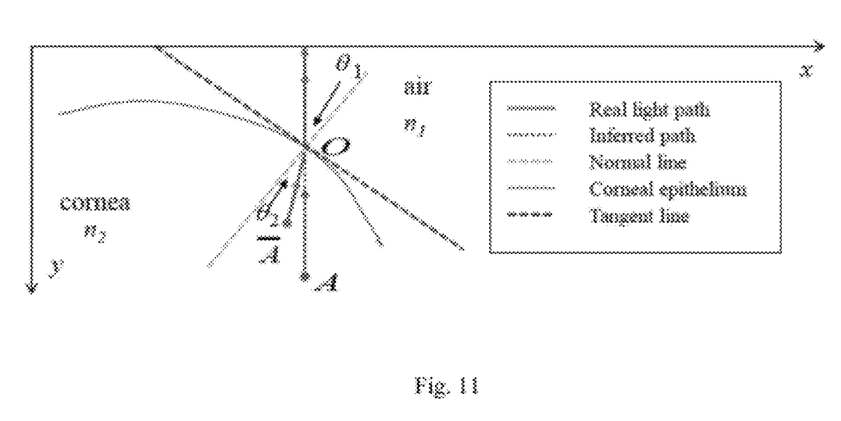
FIG. 11 illustrates a refraction correction operation sub-step of the third step of the second embodiment.

3) Refraction Correction: An AS-OCT image is distorted by refraction as the light changes direction and speed when it passes the corneal epithelium. This is illustrated in FIG. 11, which shows how the location of a light source $\overline{A}$ is different from the location A captured by the OCT system, i.e. the inferred light path by the OCT system is different from the real light path. In this step, we want to recover the location of the light source, $\overline{A}=(\overline{x},\overline{y})$, from the captured location $A=(x_r, y_r)$ in the resized image.

According to Snell's law [19]

$$\frac{\sin(\theta_1)}{\sin(\theta_2)} = \frac{n_2}{n_1}$$

where $(\theta_1, \theta_2)$ are the refraction and incident angles for the backscattered light from point $\overline{A}$ and $(n_1, n_2)$ are the refraction indices of the air and cornea respectively.

The refraction angle1 $\theta_1$ is equal to the angle between the tangent line and x-axis. Therefore $\theta_1=\arctan(q'(x_r))$ and $\theta_2=\arcsin(n_1 \sin(\theta_1)/n_2)$. The actual physical distance from the incident point $O=(x_r, q(x_r))$ to light source $\overline{A}$ is $O\overline{A}=OA \cdot n_1/n_2=|y_r-q(x_r)|n_1/n_2$.

Hence, the transformation from A to $\overline{A}$ is $$\overline{x}=F_x(x_r)=\lceil x_r-O\overline{A}\sin(\theta_1-\theta_2)\rceil \quad (11)$$

$$\overline{y}=F_y(x_r)=\lceil x_r+O\overline{A}\cos(\theta_1-\theta_2)\rceil \quad (12)$$

where $\lceil \cdot \rceil$ is the ceiling function (i.e. indicating the smallest integer which is not less than the content of the bracket). This function is used so that after the transformation, the results are integers, so that the pixels in the old image map to corresponding pixels in the dewarped image. In order to assess the anterior chamber angle, $(x_{sb}, y_{sb})$ $E_c$, $E_I$ and $M_{AC}$ are transformed to correct the distortion caused by refraction as follows:

$$(\overline{x}_{sb}, \overline{y}_{sb})=(F_x(T_x(x_{sb})), F_y(T_y(y_{sb})))$$

$$\overline{E}_c=\{(\overline{x},\overline{y})|\overline{x}=F_x(T_x(x)), \overline{y}=F_y(T_y(y)), (x,y)\in E_c\}$$

$$\overline{E}_I=\{(\overline{x},\overline{y})|\overline{x}=F_x(T_x(x)), \overline{y}=F_y(T_y(y)), (x,y)\in E_I\}$$

$$\overline{M}_{AC}=\{(\overline{x},\overline{y})|\overline{x}=F_x(T_x(x)), \overline{y}=F_y(T_y(y)), (x,y)\in M_{AC}\}.$$

1.4 Anterior Chamber Angle Assessment

Figure 12:
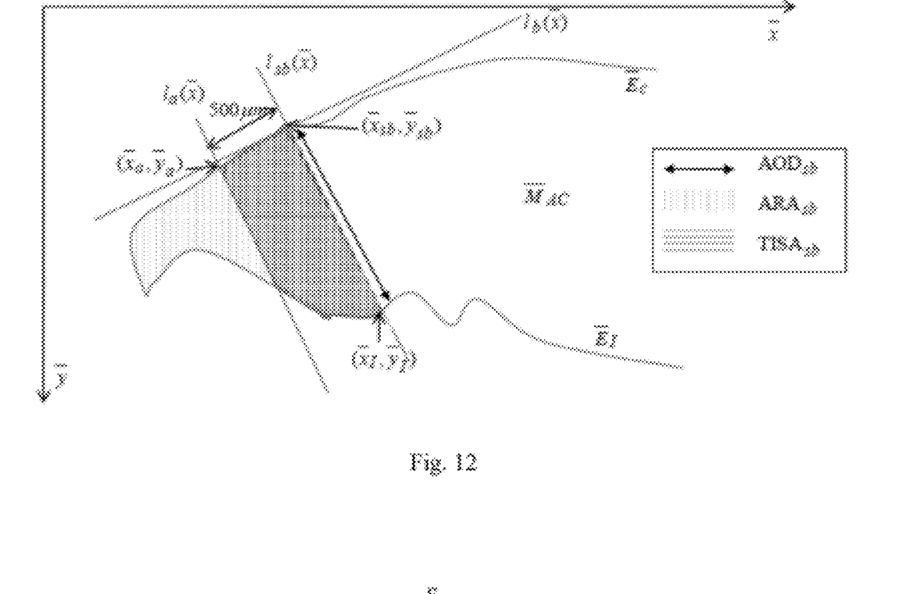
FIG. 12 illustrates a fourth step of the second embodiment.

The anterior chamber angle (ACA) measurements based on Schwalbe's line are defined as follows (see FIG. 12):

$AOD_{sb}$: The length of line segment (referred as the $AOD_{sb}$ line) drawn from Schwalbe's line $(\overline{x}_{sb},\overline{y}_{sb})_{to}$ a point $(\overline{x}_I, \overline{y}_I)$ on the anterior surface of the iris and which is perpendicular to the anterior chamber wall anterior to the Schwalbe's line.

$ARA_{sb}$: The area bounded by the angle recess, $AOD_{sb}$ line, corneal endothelium and the anterior surface of the iris.

$TISA_{sb}$: It modifies the $ARA_{sb}$ by removing the area anterior to $l_a$, which starts from point $(\overline{x}_a, \overline{y}_a)$ on the corneal endothelium and 500 μm away from the Schwalbe's line and is perpendicular to $AOD_{sb}$ line.

The calculation of the three ACA measurements is as follows ("Algorithm 4"):

Algorithm 4

1. Linear regression is used to estimate the tangent line of $E_c$ anterior to Schwalbe's line, by obtaining the line $l_c(\overline{x})=\overline{m}_c \overline{x}+\overline{b}_c$ such that:

$$(\overline{m}_c, \overline{b}_c) = \underset{(m_c, b_c)}{\operatorname{argmin}} \sum_{\overline{x}=\overline{x}_{sb}-\Delta}^{\overline{x}_{sb}} (l_c(\overline{x})-\overline{y})^2$$

2. The left and right boundaries of $TISA_{sb}$, denoted by $\overline{l}_a$ and $\overline{l}_{sb}$, and the termination point of $AOD_{sb}$ denoted by $(\overline{x}_I, \overline{y}_I)$, are calculated according to the following formulae:

$$(\overline{x}_a, \overline{y}_b) = \underset{(x,y)\in E_c}{\operatorname{argmin}} \left| \frac{w\sqrt{(\overline{x}-\overline{x}_{sb})^2+(\overline{y}-\overline{y}_{sb})^2}}{M} - 500\ \mu m \right|$$

$$\overline{l}_a(\overline{x}) = -\frac{1}{\overline{m}_c}(\overline{x}-\overline{x}_a)+\overline{y}_a$$

$$\overline{l}_{sb}(\overline{x}) = -\frac{1}{\overline{m}_c}(\overline{x}-\overline{x}_{sb})+\overline{y}_{sb}$$

$$\overline{x}_I = \max\{\overline{x}|(\overline{x},\overline{l}_{sb}(\overline{x}))\in \overline{M}_{AC}\}, \overline{y}_I=\overline{l}_c(\overline{x}_I)$$

3. Calculate $AOD_{sb}$, $ARA_{sb}$ and $TISA_{sb}$ as follows:

$$\overline{M}_{ARA} = \{(\overline{x},\overline{y})|(\overline{x},\overline{y})\in \overline{M}_{AC}, \overline{y}>\overline{l}_{sb}(\overline{x})\}$$

$$\overline{M}_{TISA} = \{(\overline{x},\overline{y})|(\overline{x},\overline{y})\in \overline{M}_{AC}, \overline{l}_{sb}(\overline{x})<\overline{y}<\overline{l}_a(\overline{x})\}$$

$$AOD_{sb} = \frac{\omega}{M}\cdot\sqrt{(\overline{x}_{sb}-x_i)^2+(\overline{y}_{sb}-y_i)^2}$$

$$ARA_{sb} = \left(\frac{\omega}{M}\right)^2|\overline{M}_{ARA}|$$

$$TISA_{sb} = \left(\frac{\omega}{M}\right)^2|\overline{M}_{TISA}|$$

Again, |•| means the cardinality.

2. Experiments and Discussion

Forty HD-OCT images captured using the Cirrus™ at the Singapore Eye Research Institute were used to test the second embodiment. The size of the test images was (M,N)=(750, 500) pixels or (924,616) pixels, and the scan dimensions are w=7.2 mm and d=2.7 mm, respectively. The test images are resized to $(\overline{M},\overline{N})$=(800,300) pixels in the dewarping process and the resolutions in transverse and axial direction are both 2.7 mm/300 pixels=9 μm. For all 40 images, we set $T_a$=50 and $T_p$=50. The processing time and the accuracy of our algorithm were evaluated.

2.1 Processing Time

The algorithm was implemented in Matlab™ R2009a using an Intel® Core™ 2 Duo CPU P7450 @ 2.13 GHz and 1.72 GHz computer. The average processing time of each stage is computed and listed as follows:

Segmentation and edge detection: 0.617 sec.
Automatic detection of Schwalbe's line: 0.055 sec.
Dewarping: 0.55 sec
Angle assessment: 0.214 sec
Total: 1.436 sec Hence, using the proposed algorithm, the operator of Cirrus™ HD-OCT can get the angle assessment measurements in 1 second without any manual labeling.

The embodiment thus simplifies the job of the ophthalmologists and saves their time.

2.2 Accuracy

As there is no existing algorithm that could detect Schwalbe's line automatically, the manual labeling is used as the ground truth to evaluate the accuracy of the second embodiment. Each original image is labeled by three ophthalmologists (i.e. three individuals who are here called BM, WHT and AT). BM did an evaluation twice), and WHT and AT each did it once. The labelings are denoted by $L_{1a}, L_{1b}, L_2$ and $L_3$, respectively. The reference point $L_0=(x_{sb}^0,y_{sb}^0)$ is the weighted average value of labelings defined by $$L_0=(0.5L_{1a}+0.5L_{1b}+L_2+L_3)/3$$

The detection error defined as $$\epsilon(\epsilon_x,\epsilon_y)=(x_{sb}-x_{sb}^0,y_{sb}-y_{sb}^0) \text{ pixels}$$

are compared with the intra-observer difference $L_{1a}-L_{1b}$ and inter-observer differences $$L_{1a}-L_0, L_{1b}-L_0, L_2-L_0 \text{ and } L_3-L_0.$$

As the detection error, inter-observer difference and intra-observer difference are vectors, the performance of the algorithm is evaluated using the first order statistics (average and standard deviation) in two directions (x and y) separately. Four statistics of the vector on forty images are defined as follows $$\mu_x(a) = \frac{1}{40}\sum_{n=1}^{40} x_a(n), \sigma_x^2(a) = \frac{1}{40}\sum_{n=1}^{40}(x_a(n)-\mu_x(a))^2,$$

$$\mu_y(a) = \frac{1}{40}\sum_{n=1}^{40} y_a(n), \sigma_y^2(a) = \frac{1}{40}\sum_{n=1}^{40}(y_a(n)-\mu_y(a))^2,$$

Where $a(n)=(x_a(n),y_a(n))$ is either the inter-observer difference, intra-observer or detection error on image n.

Overall, the results of automatic detection of Schwalbe's line are in good agreement with the ophthalmologist's labeling.

As seen from Table. 2, the mean of detection error in transversal direction $\mu_x(\epsilon)$, is smaller than that of the intra-observer difference and the inter-observer differences; and the mean of detection error in axial direction $\mu_y(\epsilon)$ is only 0.5042 pixel, which is smaller than the inter-observer differences but larger than the intra-observer difference.

TABLE 2

| | Inter-Observer differences | | | | Intra-observer difference | Detection error |
|---|---|---|---|---|---|---|
| | $L_{1a}-L_0$ | $L_{1b}-L_0$ | $L_2-L_0$ | $L_3-L_0$ | $L_{1a}-L_{1b}$ | $\epsilon$ |
| $\mu_x$ | −0.5167 | −1.1167 | 1.6833 | −0.8667 | 0.6 | 0.2912 |
| $\mu_y$ | 0.5792 | 0.5542 | −1.6458 | 1.0792 | 0.025 | −0.5042 |
| $\sigma_x$ | 5.1963 | 5.3426 | 8.3139 | 4.7807 | 3.1199 | 5.4160 |
| $\sigma_y$ | 2.1487 | 2.0119 | 2.7086 | 1.9870 | 2.0816 | 1.9213 |

Figure 13:
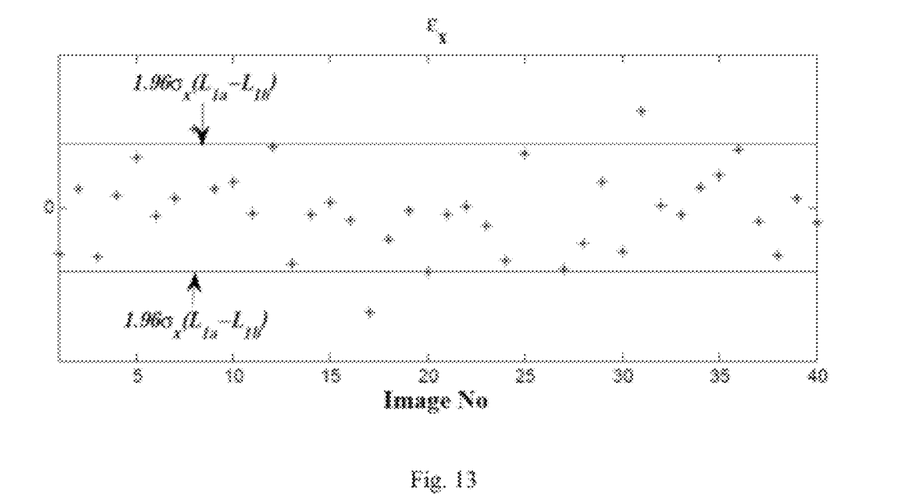
FIG. 13 illustrates experimental results from tests of the second embodiment.

In the final column of the table, the first row denotes the mean of $\epsilon_x$, the second row is the mean of $\epsilon_y$, the third row is the standard deviation of $\epsilon_x$, denoted $\sigma_x(\epsilon)$, and the last row is the standard deviation of $\epsilon_y$, denoted $\sigma_y(\epsilon)$. The reliability of our algorithm is evaluated using the standard deviation. $\sigma_y(\epsilon)$ across forty images is 1.92 pixel, which is smaller than the standard deviation of inter-observer and intra-observer differences in axial redirection. However, $\sigma_x(\epsilon)$ is 5.4160 pixel, which is a large variation as compared with that of the intra-observer difference 3.1199 pixels. It is due to the poor contrast and heavy speckle noise around the angle recess in three images. The distribution of $\epsilon_x$ is shown in FIG. 13. It can be seen that $\epsilon_x$ falls in the 95% distribution interval of intra-observer difference in 37 out of 40 images, that is the 37 images without heavy speckle noise around the angle recess. Hence, we could conclude that the accuracy of the automatic detection of Schwalbe's line algorithm is at least as good as the ophthalmologist manual labeling if there is no heavy noise around the angle recess.

We turn to an evaluation of the effect of Schwalbe's line detection error in the angle assessment. The reference point is transformed to $(\bar{x}_{sb}^0,\bar{y}_{sb}^0)$ after de-warping such that, $$(\bar{x}_{sb}^0,\bar{y}_{sb}^0)=(F_x(T_x(x_{sb}^0)),F_y(T_y(y_{sb}^0)))$$

Consequently, angle assessment measurements are computed based on the reference point and are denoted by $AOD_{sb}^0$, $ARA_{sb}^0$ and $TISA_{sb}^0$.

The performance metrics of angle assessment are defined as:

Schwalbe's line detection error after dewarping:

$$(\bar{\epsilon}_x,\bar{\epsilon}_y)=(\bar{x}_{sb}-\bar{x}_{sb}^0,\bar{y}_{sb}-\bar{y}_{sb}^0)$$
$$\text{pixels}=0.009(\bar{x}_{sb}-\bar{x}_{sb}^0,\bar{y}_{sb}-\bar{y}_{sb}^0) \text{ mm}$$

Angle assessment measurements error:

$$\epsilon_{AOD}=(AOD_{sb}^0-AOD_{sb}^0) \text{ mm}$$

$$\epsilon_{ARA}=(ARA_{sb}-ARA_{sb}^0) \text{ mm}^2$$

$$\epsilon_{TISA}=(TISA_{sb}-TISA_{sb}^0) \text{ mm}^2$$

The statistics of the performance metrics of the second embodiment are shown in Table 2. The standard deviation of the detection error in dewarped images is (4.2480,0.9380) pixels in the dewarped image, which corresponds to (0.0382, 0.0084) mm. The angle assessment measurements based on detected Schwalbe's line are quite reliable. The standard deviation of $\epsilon_{AOD}$ is 0.0048 mm, which is less than a pixel. The standard deviations of $\epsilon_{ARA}$ and $\epsilon_{TISA}$ are 0.0027 mm$^2$ and 0.0070 mm$^2$, which are 0.0252% and 0.0376% of whole image area (2.7×7.2 mm$^2$). Thereby, we could conclude that the angle assessment measurements using automatic detection of Schwalbe's line are in good agreement with the ones using the manually labeling.

Considering the cases of image containing heavy speckle around the angle recess, the second embodiment may also provide a manual labeling option, which may be used if the ophthalmologists do not agree with the automatically detected location of Schwalbe's line.

Although two embodiments of the invention have been described, many variations are possible within the scope of the appended claims. Firstly, better segmentation methods could be employed to reduce the speckle noise and eliminate the image dependant threshold value.

Another possibility is to model the lower boundary of the cornea as a piecewise linear function and investigate Finite Rate of Innovation (FRI) [22] methods to detect Schwalbe's line which appears to be the point of discontinuity. Furthermore, given that the Cirrus™ provides images at different depths of the eye, the multidimensional theoretical concepts of FRI can further be explored and applied to angle-closure glaucoma.

REFERENCES

The disclosure of the following references is incorporated herein by reference.

[1] A. Giangiacomo and A. L. Coleman, The Epidemiology of Glaucoma. Springer Berlin Heidelberg, 2009, ch. 2, pp. 13-21.
[2] Eye conditions & procedures: glaucoma. Singapore National Eye Center. [Online]. Available: http://www.snec.com/sg/eye/glaucoma.asp
[3] Closed-angle glaucoma. Centra Health Care System. [Online]. Available: http://www.centracare.com/index.html
[4] A. Dellaport, "Historical notes on gonioscopy," Survey of Ophthalmology, vol. 20, pp. 137-149, 1975.
[5] D. S. Friedman and H. Mingguang, "Anterior chamber angle assessment techniques," Survey of Ophthalmology, vol. 53, no. 3, pp. 250-273, 2007.
[6] C. Pavlin, M. Sherar, and F. F S, "Subsurface ultrasound microscopic imaging of the intact eye," Ophthalmology, vol. 97, no. 2, pp. 244-250, February 1990.
[7] C. J. Pavlin, K. Harasiewicz, M. D. Sherar, and F. S. Foster, "Clinical use of ultrasound biomicroscopy," Ophthalmology, vol. 98, no. 3, pp. 287-295, March 1991.
[8] G. Spaeth, A. Aruajo, and A. Azuara, "Comparison of the configuration of the human anterior chamber angle, as determined by the spaeth goioscopic grading system and ultrasound biomicroscopy," Transactions of American Ophthalmological Society, vol. 93, pp. 337-347, 1995.
[9] H. Ishikawa, K. Esaki, L. J M, Y. Uji, and R. Ritch, "Ultrasound biomicroscopy dark room provocative testing: a quantitative method for estimating anterior chamber angle width," Japanese Journal of Ophthalmology, vol. 43, no. 6, pp. 526-534, November-December 1999.
[10] W. P. Nolan, J. L. See, P. T. Chew, D. S. Friedman, S. D. Smith, S. Radhakrishnan, C. Zheng, P. J. Foster, and T. Aung, "Detection of primary angle closure using anterior segment optical coherence tomography in asian eyes," Ophthalmology, vol. 114, no. 1, pp. 33-39, January 2007.
[11] J. W. Console, L. M. Sakata, T. Aung, D. S. F. Man, and M. He, "Quantitative analysis of anterior segment optical coherence tomography images: the Zhongshan Angle Assessment Program," British Journal of Ophthalmology, vol. 92, pp. 1612-1616, 2008.
[12] The certainty of Cirrus. Carl Zeiss Meditec. [Online]. Available: http://www.cirrusoctdemo.com/index.html
[13] Visante omni: A new dimension in anterior segment evaluation, Zeiss.
[14] Cirrus HD-OCT User Manual Addendum-Anterior Segment Imaging, Zeiss.
[15] H.-T. Wong, M. C. Lim, L. M. Sakata, H. T. Aung, N. Amerasinghe, D. S. Friedman, and T. Aung, "High-definition optical coherence tomography imaging of the iridocorneal angle of the eye," Clinical Sciences, vol. 127, no. 3, pp. 256-260, 2009.
[16] P. Soille, Morphological Image Analysis; Principles and Applications. Springer-Verlag Telos, 2003.
[17] H. Samet and M. Tamminen, "Efficient component labeling of images of arbitrary dimension represented by linear bintrees." IEEE Transactions on Pattern Analysis and Machine Intelligence, vol. 10, pp. 579-586, 1988.
[18] V. Westphal, A. M. Rollins, and S. Radhakrishnan, "Correction of geometric and refractive image distortions in optical coherence tomography applying Fermat's principle," OPTICS EXPRESS, vol. 10, no. 9, pp. 397-404, 2002.
[19] L. S. Lerner, Physics for scientists and engineers. Jones and Bartlett Publishers, 1996.
[20] S. Radhakrishnan, J. Goldsmith, D. Huang, V. Westphal, D. K. Dueker, A. M. Rollins, J. A. Izatt, and S. D. Smith, "Comparison of optical coherence tomography and ultrasound biomicroscopy for detection of narrow anterior chamber angles," Archives of Ophthalmology, vol. 123, pp. 1053-1059, 2005.
[21] N. Otsu, "A threshold selection method from gray-level histograms," IEEE Transactions on Systems, Man, and Cybernetics, vol. 9, pp. 62-66, 1979.
[22] M. Vetterli, P. Marziliano, and T. Blu, "Sampling signals with finite rate of innovation," IEEE Transactions on Signal Processing, vol. 50, no. 6, pp. 1417-1428, June 2002.

The invention claimed is:

1. A computational method of analyzing a pixilated optical coherence tomography (OCT) image of the anterior chamber of an eye and treating the eye, the method comprising automatically detecting a location in the image corresponding to Schwalbe's line by:
    (a) detecting the location in the image of the corneal endothelium;
    (b) fitting a model to the detected corneal endothelium; and
    (c) determining the location in the image corresponding to Schwalbe's line according to the divergence between the detected corneal endothelium and the fitted model; and
    (d) treating the eye for glaucoma.

2. The computational method of claim 1 in which the model of the detected corneal endothelium is a 4-th order polynomial equation.

3. The computational method of claim 1 in which said step of determining the location in the image corresponding to Schwalbe's line is performed by determining the location at which the detected corneal endothelium diverges maximally from the fitted model.

4. The computational method of claim 1 in which said step of determining the location in the image corresponding to Schwalbe's line comprises:
    identifying a window region within which the detected corneal endothelium diverges from the fitted model to a first side of the fitted model; and
    determining said location in the image corresponding to Schwalbe's line as a location within said window region.

5. The computational method of claim 4 in which said step of determining said location within said window region comprises fitting a second model of the corneal endothelium to a portion of the detected corneal endothelium outside the window, and finding where the detected corneal endothelium diverges maximally from the second model within the window.

6. The computational method of claim 1 in which the step of detecting the location of the corneal endothelium comprises:
    (i) thresholding the OCT image, to identify first pixels having an intensity above a threshold and second pixels having an intensity below the threshold;
    (ii) detecting connected groups of the first pixels;
    (iii) comparing the respective sizes of the connected groups of the first pixels to determine whether the largest said connected group of the first pixels comprises pixels representative of an iris of the eye,
    said step of detecting the corneal endothelium being performed by different sub-steps according to whether the determination is positive.

7. The computational method of claim 6 in which, if the determination is negative, the corneal endothelium is detected as part of an edge of said largest connected group of first pixels, and if the determination is positive, the corneal endothelium is detected as part of an edge of a connected group of said second pixels.

8. The computational method of claim 1 further comprising performing regression on a part of the detected corneal endothelium selected based on the determined location in the image corresponding to Schwalbe's line, to obtain a first regression line, and using the first regression line to obtain at least one measure of an anterior chamber angle.

9. The computational method of claim 8 in which said at least one measure of the anterior chamber angle is an area of a portion of a connected group of pixels having an intensity in the image below a threshold, said portion being selected using the detected location corresponding to Schwalbe's line.

10. The computational method of claim 8 in which said step of obtaining at least one measure of the anterior chamber angle comprises detecting an edge of the iris facing the corneal endothelium, said at least one measure of the anterior chamber angle comprising a said measure which is the size of an area bounded by the first regression line, said edge of the iris, and a line generated based on said detected location corresponding to Schwalbe's line.

11. The computational method of claim 1 further comprising correcting said image for refraction distortion by a step of transforming the image according to a transform based on an estimate of a line in the image corresponding to the corneal epithelium, said estimate of the line in the image corresponding to the corneal epithelium being generated automatically from said image.

12. The computational method claim 11 in which said estimate of the line in the image corresponding to the corneal epithelium is generated automatically by thresholding the image, obtaining an edge of a connected group of pixels in the thesholded image, and fitting the edge to a numerical model of the corneal epithelium.

13. The computation method of claim 12 in which, before the numerical model of the corneal epithelium is fitted to the edge, any pixels of the connected group of pixels associated with roughness are removed from the connected group of pixels.

14. A method for treating a set of subjects of whom at least one is subject to glaucoma, the method comprising:
  capturing at least one respective pixilated optical coherence tomography (OCT) image of the anterior chamber of an eye of each said subject;
  identifying one of more of said subjects who have a reduced anterior chamber angle by, for each said image:
  (a) detecting the location in the image of the corneal endothelium;
  (b) fitting a model to the detected corneal endothelium;
  (c) determining a location in the image corresponding to Schwalbe's line according to the divergence between the detected corneal endothelium and the fitted model; and
  (d) using the determined location in the image corresponding to Schwalbe's line, to obtain at least one measure of said anterior chamber angle; and
  treating at least one of said identified subjects for glaucoma.

15. An computational system for analysing a pixilated optical coherence tomography (OCT) image of the anterior chamber of an eye, the apparatus comprising a processor, and a tangible data storage device, the data storage device storing computer program instructions operative, when implemented by the processor, to cause the processor to automatically detect a location in the image corresponding to Schwalbe's line by:
  (a) detecting the location in the image of the corneal endothelium;
  (b) fitting a model to the detected corneal endothelium; and
  (c) determining the location in the image corresponding to Schwalbe's line according to the divergence between the detected corneal endothelium and the fitted model; and
  (d) outputting data indicative of a required treatment of the eye for glaucoma.

* * * * *